United States Patent
Iwayasu et al.

(10) Patent No.: US 7,759,003 B2
(45) Date of Patent: Jul. 20, 2010

(54) POLYMERIZABLE BORIC COMPOUNDS, METHODS OF PRODUCING THE SAME, POLYMERIZABLE COMPOSITIONS AND IONIC-CONDUCTIVE POLYMERIC ELECTROLYTES

(75) Inventors: Norio Iwayasu, Hitachinaka (JP); Shin Nishimura, Hitachi (JP); Takefumi Okumura, Hitachinaka (JP); Tetsuya Itoh, Kamakura (JP); Takeshi Yabe, Kawasaki (JP)

(73) Assignee: Hitachi, Ltd., Tokyo (JP)

( * ) Notice: Subject to any disclaimer, the term of this patent is extended or adjusted under 35 U.S.C. 154(b) by 1251 days.

(21) Appl. No.: 11/300,307

(22) Filed: Dec. 15, 2005

(65) Prior Publication Data

US 2006/0147805 A1   Jul. 6, 2006

(30) Foreign Application Priority Data

Dec. 17, 2004   (JP) .............................. 2004-365760

(51) Int. Cl.
*H01M 6/04*   (2006.01)

(52) U.S. Cl. ....................... 429/188; 429/189; 429/317; 252/62.2

(58) Field of Classification Search ................. 429/188, 429/189, 317; 252/62.2
See application file for complete search history.

(56) References Cited

U.S. PATENT DOCUMENTS 6,998,465 B2 *   2/2006   Yokoyama et al. .......... 528/394

\* cited by examiner

*Primary Examiner*—Laura S Weiner
(74) *Attorney, Agent, or Firm*—Antonelli, Terry, Stout & Kraus, LLP.

(57) ABSTRACT

A polymerizable boric compound for electrochemical devices represented by the formula (1), wherein, B represents a boron atom, Z represents a polymerizable functional group, X represents a divalent $C_{1-12}$ hydrocarbon group or in the absence of X, Z and B form a direct bond, AO represents a $C_{2-4}$ oxyalkylene group, m and n are each the number of moles of the oxyalkylene group added and each independently stands for 2 or greater but less than 6, and $R^1$ and $R^2$ each represents a $C_{1-12}$ hydrocarbon group.

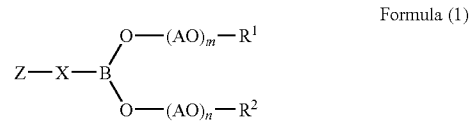

Formula (1)

10 Claims, 1 Drawing Sheet

POLYMERIZABLE BORIC COMPOUNDS, METHODS OF PRODUCING THE SAME, POLYMERIZABLE COMPOSITIONS AND IONIC-CONDUCTIVE POLYMERIC ELECTROLYTES

CLAIM OF PRIORITY

This application claims priority from Japanese application serial No. 2004-365760, filed on Dec. 17, 2004, the content of which is hereby incorporated by reference into this application.

FIELD OF THE INVENTION

The present invention relates to polymerizable boric compounds for electrochemical devices, methods of producing the same, polymerizable compositions, and ionic-conductive polymer electrolytes.

BACKGROUND OF THE INVENTION

For electrolytes constituting electrochemical devices such as batteries, capacitors and sensors, liquid electrolytes have conventionally been used from the viewpoint of ionic conductivity. They had however problems such as fear of these devices being damaged by liquid leak.

In order to overcome such a problem, secondary batteries using a solid electrolyte such as inorganic crystalline material, inorganic glass or organic polymer have recently been proposed. Compared with the use of a conventional liquid electrolyte employing a carbonate solvent, use of such a solid electrolyte improves reliability and safety of the device because it is free from the leak problem of the carbonate solvent and enables reduction in ignition property to an electrolyte.

Since organic polymers usually have excellent workability and moldability or formability, can provide an electrolyte equipped with flexibility and bending property and heighten freedom of design of the device to which the resulting electrolyte is applied, they are expected as a promising material.

Polymer electrolytes obtained by incorporating a specific alkali metal salt in the organic polymers as described above, for example, polyethylene oxide however have an ionic conductivity lower than that of the liquid electrolytes and are therefore inferior thereto (for example, Z. Stoeva et al., J. Am. Chem. Soc. 125, 4619 (2003)).

In addition, in the polymer electrolytes, the alkali metal salt incorporated therein dissociates into a cation portion and an anion portion and respective ions transfer, but their selectivity plays an important factor. In particular, when polymer electrolytes are applied to lithium ion batteries, a higher transference number of lithium ions is desired. Improvement in the transference number of lithium ions however decreases ionic conductivity, making it difficult to apply it to lithium ion batteries (for example, M. A. Mehta, et al., J. Power Sources, 81-82, 724 (1999).

An object of the present invention is to provide an ionic-conductive polymer electrolyte satisfactory in both ionic conductivity and transference number of lithium ion and a novel polymerizable boric compound useful as a raw material for the ionic-conductive polymer electrolyte.

SUMMARY OF THE INVENTION

In the present invention, there are thus provided a polymerizable boric compound represented by the below-described formula (1) and an ionic-conductive polymer electrolyte.

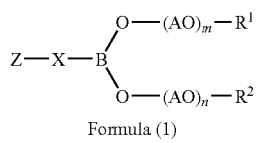

Formula (1)

[Chemical formula 1]

Use of the above-described compound or ionic-conductive polymer electrolyte containing a polymer available by polymerizing a polymerizable composition containing the compound decreases the number of moles of oxyalkylene groups added, facilitates transfer of lithium ions forming a coordinate bond to ether oxygen, and heightens ionic conductivity. In addition, a boron atom is fixed to a polymer matrix so that the transference number of cation increases.

DETAILED DESCRIPTION OF PREFERRED EMBODIMENTS

Figure 1:
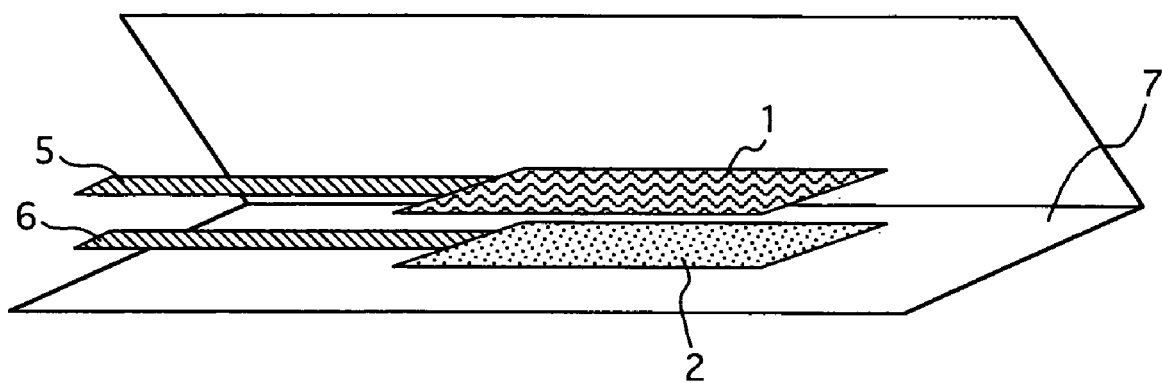
FIG. 1 is an expanded perspective view illustrating the constitution of a lithium second battery for test using the polymer electrolyte of the present invention.

In the formula (1), Z represents a polymerizable functional group, for example, a group having a polymerizable double bond such as vinyl, allyl, methallyl, acryloyl or methacryloyl. By selecting a group having a polymerizable double bond and carrying out polymerization, an ionic-conductive polymer or polymer electrolyte is available. Of the above-described groups, vinyl, acryloyl and methacryloyl groups are preferred because each of them can form a polymer readily by radical polymerization.

The above-described polymerizable boric compound for electrochemical devices can be produced by reacting a compound of the formula (2) with compounds of the formulas (3) and (4).

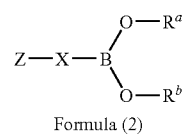

Formula (2)

[Chemical formula 2]

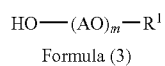 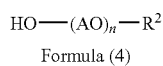

Formula (3)  Formula (4)

[Chemical formula 3]

In the formula, B represents a boron atom, Z represents a polymerizable functional group, X may be present or absent and represents a divalent $C_{1-12}$ hydrocarbon group, or in the absence of X, Z and B form a direct bond, $R^a$ and $R^b$ each independently represents a $C_{1-24}$ hydrocarbon group or a hydrogen atom, AO represents a $C_{2-4}$ oxyalkylene group, m and n each independently stands for 2 or greater but less than 6, and $R^1$ and $R^2$ represents a $C_{1-12}$ hydrocarbon group, with the proviso that the formula (3) and the formula (4) may be the same or different.

In the above-described producing method, it is preferred to select the conditions under which the total amount of the compounds of the formula (3) and formula (4) is from 1.5 to 2.1 moles per mole of the compound of the formula (2), and the reaction temperature falls within a range of from 0 to 100° C.

In the formula (1), (3) or (4), $R^1$ and $R^2$ each represents a $C_{1-12}$ hydrocarbon group. Examples of the $C_{1-12}$ hydrocarbon group include aliphatic hydrocarbon groups such as methyl, ethyl, propyl, isopropyl, butyl, isobutyl, t-butyl, pentyl, hexyl, heptyl, octyl, isooctyl, nonyl, decyl, undecyl and dodecyl, aromatic hydrocarbon groups such as phenyl, toluyl and naphthyl, and alicyclic hydrocarbon groups such as cyclopentyl, cyclohexyl, methylcyclohexyl and dimethylcyclohexyl. Of these hydrocarbon groups, those having 4 or less carbon atoms are preferred because they can increase the solubility of the electrolytic salt, with a methyl group which is a $C_1$ hydrocarbon group being more preferred. $R^1$ and $R^2$ may be the same or different.

In the formula (1) or (2), X represents a $C_{1-12}$ hydrocarbon group. When X is absent, B and Z form a direct bond. Examples of the $C_{1-12}$ hydrocarbon group include aliphatic hydrocarbon groups such as methylene, ethylene, propylene, isopropylene, butylene, isobutylene, dimethylethylene, pentylene, hexylene, heptylene, octylene, isooctylene, decylene, undecylene, and dodecylene, alicyclic hydrocarbon groups such as cyclohexylene and dimethylcyclohexylene, and aromatic hydrocarbon groups such as phenylene, 2-methylphenylene, 2,6-dimethylphenylene and 2-ethylphenylene. In order to increase a boron concentration to heighten the transference number of cation, $C_{1-8}$ hydrocarbon groups are preferred, with $C_{1-4}$ hydrocarbon groups being more preferred.

In the formula (1), (3) or (4), AO represents a $C_{2-4}$ oxylakylene group such as oxyethylene, oxypropylene oxybutylene or oxytetramethylene. Use of an oxyethylene or oxypropylene group is preferred because it can heighten the ionic conductivity.

In the formula (1), (3) or (4), m and n each represents the number of moles of an oxyalkylene group added and each independently stands for 2 or greater but less than 6. When m or n exceeds 6, mutual action with cation due to ether oxygen becomes large, leading to reduction in ionic conductivity.

The polymerizable boric compound of the formula (1) can be produced in the following manner. It is available by adding a polyalkylene glycol monoether represented by the formula (3) or (4) to a boric compound of the formula (2) having a polymerizable functional group and reacting the mixture while feeding with dry air or nitrogen.

The total amount of the polyalkylene glycol monoethers represented by the formulas (3) and (4) falls within a range of from 1.5 to 2.1 moles per mole of the boric compound of the formula (2) having a polymerizable functional group. In order to produce the polymerizable boric compound of the formula (1) according to the present invention in a high yield, the total amount of the polyalkylene glycol monoethers represented by the formulas (3) and (4) preferably falls within a range of from 1.8 to 2.1 moles.

The compound of the formula (1) is produced by the reaction between the compound of the formula (2) and the compounds of the formulas (3) and (4). The above-described reaction is an equilibrium reaction so that the reaction proceeds by the removal of the reaction by-product of the formula (5). When the compound to be eliminated is water ($R^a$, $R^b$: H), it can be eliminated by using toluene as a reaction solvent and utilizing azeotropy between the toluene and water. When the compound to be eliminated is an alcohol ($R^a$, $R^b$: hydrocarbon group), it is volatilized by vacuuming in an azeotropic mixture system by making use of a difference in boiling point and eliminated from the reaction system. When the compound to be eliminated is an alcohol, a reaction solvent such as toluene can also be used. The reaction temperature is from 0 to 100° C., with from 0 to 80° C. being preferred for the purpose of avoiding initiation of polymerization of the polymerizable functional group which will otherwise occur owing to thermal history.

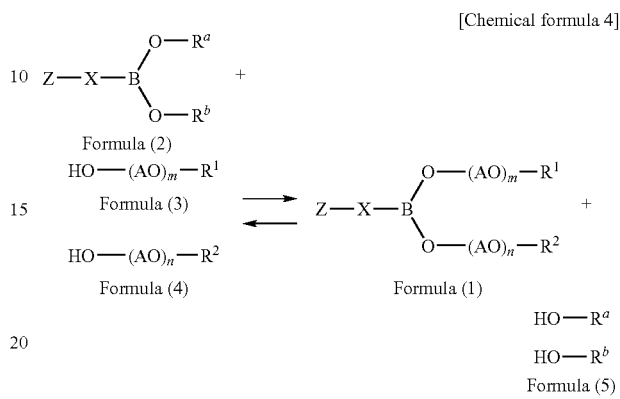

[Chemical formula 4]

wherein, the formula (2): a boric compound having a polymerizable functional group (in which B represents a boron atom, Z represents a polymerizable functional group, X represents a divalent $C_{1-12}$ hydrocarbon group or phenylene group, or in the absence of X, Z and B form a direct bond, and $R^a$ and $R^b$ each independently represents a $C_{1-24}$ hydrocarbon group or hydrogen atom), the formulas (3) and (4): polyalkylene glycol monoethers (in which AO represents a $C_{2-4}$ oxyalkylene group, m and n each independently stands for 2 or greater but less than 6, and $R^1$ and $R^2$ each represents a $C_{1-12}$ hydrocarbon group, with the proviso that the formulas (3) and (4) may be the same or different), the formula (1): polymerizable boric compound, and the formula (5): water or alcohol.

The polymerizable boric compound of the formula (1) may be polymerized by any one of the conventionally known methods, that is, bulk polymerization, solution polymerization and emulsion polymerization. Another polymerization compound may be used in combination. Examples of the another polymerizable compound include compounds having a (meth)acrylate group, vinyl group or allyl group. From the viewpoints of handling ease and contribution to ionic conductivity, (meth)acrylate compounds and polyalkylene glycol (meth)acrylate compounds are preferred. A polymerization initiator is not indispensable for effecting polymerization. From the viewpoint of handling ease, use of a radical polymerization initiator is preferred.

Polymerization in the presence of a radical polymerization initiator can be carried out while employing ordinarily employed conditions in temperature range and polymerization time. In order not to impair members to be used for an electrochemical device, it is preferred to use a radical polymerization initiator having from 30 to 90° C. as a range of 10-hour half-life temperature which is an indicator of decomposition temperature and rate. The term "10-hour half-life temperature" means a temperature necessary for reduction, by half, of the amount of an undecomposed radical polymerization initiator having a concentration of 0.01 mole/liter in a radical inert solvent such as benzene in 10 hours. The amount of the initiator in the present invention is 0.01 mol % or greater but not greater than 10 mol %, preferably 0.1 mol % or greater but not greater than 5 mol %, per mol of the polymerizable functional group.

Examples of the radical polymerization initiators include organic peroxides such as t-butyl peroxypivalate, t-hexyl peroxypivalate, methyl ethyl ketone peroxide, cyclohexanone peroxide, 1,1-bis(t-butylperoxy)-3,3,5-trimethylcyclohexane, 2,2-bis(t-butylperoxy)octane, n-butyl-4,4-bis(t-butylperoxy)valerate, t-butyl hydroperoxide, cumene hydroperoxide, 2,5-dimethylhexane-2,5-dihydroperoxide, di-t-butyl peroxide, t-butylcumyl peroxide, dicumyl peroxide, a,a'-bis(t-butylperoxy-m-isopropyl)benzene, 2,5-dimethyl-2,5-di(t-butylperoxy)hexane, benzoyl peroxide and t-butylperoxyisopropyl carbonate, and azo compounds such as 2,2'-azobisisobutyronitrile, 2,2'-azobis(2-methylbutyronitrile), 2,2'-azobis(4-methoxy-2,4-dimethylvaleronitrile), 2,2'-azobis(2,4-dimethylvaleronitrile), 1,1'-azobis(cyclohexane-1-carbonitrile), 2-(carbamoylazo)isobutyronitrile, 2-phenylazo-4-methoxy-2,4-dimethyl-valeronitrile, 2,2'-azobis(2-methyl-N-phenylpropionamidine) dihydrochloride, 2,2'-azobis[N-(4-chlorophenyl)-2-methylpropionamidine] dihydrochloride, 2,2'-azobis[N-hydroxyphenyl]-2-methylpropionamidine]dihydrochloride, 2,2'-azobis[2-methyl-N-(phenylmethyl)propionamidine]dihydrochloride, 2,2'-azobis[2-methyl-N-(2-propenyl)propionamidine]dihydrochloride, 2,2'-azobis(2-methylpropionamidine) dihydrochloride, 2,2'-azobis[N-(2-hydroxyethyl)-2-methylpropionamidine]dihydrochloride, 2,2'-azobis[2-(5-methyl-2-imidazolin-2-yl)propane]dihydrochloride, 2,2'-azobis[2-(2-imidazolin-2-yl)propane]dihydrochloride, 2,2'-azobis[2-(4,5,6,7-tetrahydro-1H-1,3-diazepin-2-yl)propane] dihydrochloride, 2,2'-azobis[2-(3,4,5,6-tetrahydropyrimidin-2-yl)propane]dihydrochloride, 2,2'-azobis[2-(5-hydroxy-3,4,5,6-tetrahydropyrimidin-2-yl) propane]dihydrochloride, 2,2'-azobis{2-[1-(2-hydroxyethyl)-2-imidazolin-2-yl]propane}dihydrochloride, 2,2'-azobis[2-(2-imidazolin-2-yl]propane], 2,2'-azobis{2-methyl-N-[1,1-bis(hydroxymethyl)-2-hydroxyethyl] propionamide}, 2,2'-azobis{2-methyl-N-[1,1-bis (hydroxymethyl)ethyl]propionamide}, 2,2'-azobis[2-methyl-N-(2-hydroxyethyl)propionamide], 2,2'-azobis(2-methylpropionamide)dihydrate, 2,2'-azobis(2,4,4-trimethylpentane), 2,2'-azobis(2-methylpropane), dimethyl 2,2'-azobisisobutyrate and 4,4'-azobis (4-cyanovaleric acid), and 2,2'-azobis[2-(hydroxymethyl)propionitrile].

Although no particular limitation is imposed on the electrolytic salts used in the present invention insofar as they are soluble in the polymerizable boric compound of the present invention or polymer obtained by polymerizing the compound, following ones are preferred. Examples include compounds composed of a metallic cation and an anion selected from chloride ion, bromide ion, iodide ion, perchlorate ion, thiocyanate ion, tetrafluoroborate ion, hexafluorophosphate ion, trifluoromethanesulfonideimidate ion, stearylsulfonate ion, octylsulfonate ion, dodecylbenzenesulfonate ion, naphthalenesulfonate ion, dodecylnapthalenesulfonate ion, 7,7,8,8-tetracyano-p-quinodimethane ion, and lower aliphatic carboxylate ions. Examples of the metallic cation include Li, Na, K, Rb, Cs, Mg, Ca and Ba metallic ions.

Concentration of the electrolyte preferably falls within a range of from 0.0001 to 1, more preferably from 0.001 to 0.5 as a molar ratio based on the number of moles of ether oxygen atoms contained in the oxyalkylene group of the ion-conductive polymer, namely, (the number of moles of electrolytic salt)/(total number of moles of ether oxygen atoms contained in an oxyalkylene group). Molar ratios exceeding 1 lead to deteriorations in the workability, moldability or formability and mechanical strength of the resulting polymer electrolyte.

Examples of the plasticizer in the present invention include organic solvents employed for electrolytes for lithium batteries such as diethyl carbonate, dimethyl carbonate, ethylene carbonate, propylene carbonate, γ-butyrolactone, tetrahydrofuran and dimethoxyethane, and borate ester compounds. By adding such a compound to an ion-conductive polymer electrolyte, physical properties of the electrolyte can be controlled as needed.

Examples of the reinforcing material in the present invention include fibrous glass cloth using glass fibers, nonwoven fabric made of polyolefin, polyester or the like, and separators for lithium ion batteries. Any material can be used insofar as it is a reinforcing material not adversely affecting lithium batteries. Use of the reinforcing material increases the mechanical strength, enabling film thinning of ion-conductive polymer electrolytes.

The polymer electrolyte according to the present invention is very useful as an electrolyte for secondary batteries, especially useful as electrolyte for lithium secondary batteries.

EXAMPLES

The present invention will hereinafter be described more specifically by examples. It should however be borne in mind that the present invention is not limited to or by them. In the examples, preparation of samples and evaluation of ionic conductivity were all carried out in an argon atmosphere. Moreover, in all the examples and comparative examples, concentration of the electrolytic salt was adjusted so that the molar ratio based on the total number of moles of ether oxygen atoms in the oxyalkylene group in the ion-conductive polymer, that is, (the number of moles of electrolytic salt)/(total number of moles of ether oxygen atoms in oxyalkylene group) be 0.03. The examples and the comparative examples in the present invention are listed in Table 1.

Method of Evaluation

<Ionic conductivity> The ionic conductivity was measured by an alternating current impedance method which comprises putting a polymer electrolyte between stainless steel electrodes at 25° C. to construct an electrochemical cell and applying an alternating current between the electrodes, and measuring the resistant components, and the ionic conductivity was calculated from real-number impedance intercept in a Cole-Cole plot.

<Transference number of lithium ion> The polymer electrolytes obtained in the below-described Examples 1 to 7 and Comparative Examples 1 and 2 were each sandwiched between lithium metals and the transference number of lithium ion was measured in accordance with the method as described in J. Evans, et. al., Polymer, 28, 2324 (1987). The results are shown in Table 1.

Example 1

To 504 g (2.0 mol) of pentaethylene glycol monomethyl ether was added 184 g (1.0 mol) of dibutyl vinyl borate (product of Aldrich) from which a polymerization inhibitor had been removed by distillation, followed by stirring at room temperature for 30 minutes. After the pressure in the system was reduced to 0.4 kPA, the temperature was raised to 55° C. Stirring was continued for 3 hours to remove eliminating butanol, whereby 432 g of a polymerizable boric compound A represented by the formula (1) (X: absent, m and n=5, $R^1$ and $R^2$=methyl group) was obtained. As a result of observation by infrared absorption spectrometry, an absorption band originating from hydroxyl group at 3300 cm$^{-1}$ disappeared, from which the existence of the resulting polymerizable boric compound A was confirmed.

A polymerizable composition was obtained by mixing 5.40 g (10 mmol) of the polymerizable boric compound A, 5.40 g of 2,2'-azobisisobutyronitrile and LiN(CF$_3$SO$_2$)$_2$ as an electrolytic salt. The resulting solution was poured into a boat made of polytetrafluoroethylene and kept at 80° C. for 3 hours to obtain a polymer electrolyte of 0.1 mm thickness. The film of the electrolyte thus obtained was cut into a disc of 1 cm in diameter, and put between a pair of stainless steel electrodes. The ionic conductivity was then determined by the above-described measuring method of ionic conductivity at 25° C. The ionic conductivity was found to be 0.5 mS/cm.

Example 2

To 328 g (2.0 mol) of triethylene glycol monomethyl ether was added 184 g (1.0 mol) of dibutyl vinyl borate (product of Aldrich) from which a polymerization inhibitor had been removed by distillation, followed by stirring at room temperature for 30 minutes. After the pressure in the system was reduced to 0.4 kPA, the temperature was raised to 60° C. Stirring was continued for 3 hours to remove eliminating butanol, whereby 273 g of a polymerizable boric compound B represented by the formula (1) (X: absent, m and n=3, $R^1$ and $R^2$=methyl group) was obtained. As a result of observation by infrared absorption spectrometry, an absorption band originating from hydroxyl group at 3300 cm$^{-1}$ disappeared, from which the existence of the resulting polymerizable boric compound B was confirmed.

A polymerizable composition was obtained by mixing 3.64 g (10 mmol) of the polymerizable boric compound B, 3.64 mg of 2,2'-azobisisobutyronitrile and LiN(CF$_3$SO$_2$)$_2$ as an electrolytic salt. The resulting solution was poured into a boat made of polytetrafluoroethylene and kept at 80° C. for 3 hours to obtain a polymer electrolyte of 0.1 mm thickness. The film of the electrolyte thus obtained was cut into a disc of 1 cm in diameter, and put between a pair of stainless steel electrodes. The ionic conductivity was then determined by the above-described measuring method of ionic conductivity at 25° C. The ionic conductivity was found to be 1.0 mS/cm.

Example 3

To 504 g (2.0 mol) of pentaethylene glycol monomethyl ether was added 148 g (1.0 mol) of 4-vinylphenyl boric acid (product of Aldrich), followed by the addition of toluene as a solvent. After the pressure in the system was reduced to 8 kPA, the temperature was raised to 55° C. Stirring was continued for 5 hours under toluene reflux to remove water which was a reaction by-product. The toluene as a solvent was then distilled off, whereby 246 g of a polymerizable boric compound C represented by the formula (1) (X=phenylene, m and n=5, $R^1$ and $R^2$=methyl group) was obtained. As a result of observation by infrared absorption spectrometry, an absorption band originating from hydroxyl group at 3300 cm$^{-1}$ disappeared, from which the existence of the resulting polymerizable boric compound C was confirmed.

A polymerizable composition was obtained by mixing 6.16 g (10 mmol) of the polymerizable boric compound C, 6.16 mg of 2,2'-azobisisobutyronitrile and LiN(CF$_3$SO$_2$)$_2$ as an electrolytic salt. The resulting solution was poured into a boat made of polytetrafluoroethylene and kept at 100° C. for 3 hours to obtain a polymer electrolyte of 0.1 mm thickness. The film of the electrolyte thus obtained was cut into a disc of 1 cm in diameter, and put between a pair of stainless steel electrodes. The ionic conductivity was then determined by the above-described measuring method of ionic conductivity at 25° C. The ionic conductivity was found to be 0.08 mS/cm.

Example 4

To 328 g (2.0 mol) of triethylene glycol monomethyl ether was added 148 g (1.0 mol) of 4-vinylphenyl boric acid (product of Aldrich), followed by the addition of toluene as a solvent. After the pressure in the system was reduced to 8 kPA, the temperature was raised to 55° C. Stirring was continued for 5 hours to remove water which was a reaction by-product. The toluene as a solvent was then distilled off, whereby 220 g of a polymerizable boric compound D represented by the formula (1) (X=phenylene, m and n=3, $R^1$ and R=methyl group) was obtained. As a result of observation by infrared absorption spectrometry, an absorption band originating from hydroxyl group at 3300 cm$^{-1}$ disappeared, from which the existence of the resulting compound D was confirmed.

A polymerizable composition was obtained by mixing 4.40 g (10 mmol) of the polymerizable boric compound D, 4.40 mg of 2,2'-azobisisobutyronitrile and LiN(CF$_3$SO$_2$)$_2$ as an electrolytic salt. The resulting solution was poured into a boat made of polytetrafluoroethylene and kept at 100° C. for 3 hours to obtain a polymer electrolyte of 1 mm thickness. The film of the electrolyte thus obtained was cut into a disc of 1 cm in diameter, and put between a pair of stainless steel electrodes. The ionic conductivity was then determined by the above-described measuring method of ionic conductivity at 25° C. The ionic conductivity was found to be 0.05 mS/cm.

Example 5

As in Example 4, a polymerizable composition solution was obtained by adding 0.5 g of propylene carbonate to a solution obtained by mixing 4.40 g (10 mmol) of the polymerizable compound D, 4.40 mg of 2,2'-azobisisobutyronitrile and LiN(CF$_3$SO$_2$)$_2$. The resulting solution was poured into a boat made of polytetrafluoroethylene and kept at 100° C. for 3 hours to obtain a polymer electrolyte of 1 mm thickness. The film of the electrolyte thus obtained was cut into a disc of 1 cm in diameter, and put between a pair of stainless steel electrodes. The ionic conductivity was then determined by the above-described measuring method of ionic conductivity at 25° C. The ionic conductivity was 0.4 mS/cm.

Example 6

As in Example 4, a polymerizable composition solution was obtained by mixing 4.40 g (10 mmol) of the polymerizable compound D, 4.40 mg of 2,2'-azobisisobutyronitrile and LiN(CF$_3$SO$_2$)$_2$. With the resulting solution, a glass cloth (50 μm thickness) to be used as a reinforcing material was impregnated and the resulting cloth was maintained at 100° C. for 3 hours, whereby a polymer electrolyte of 70 μm thickness was obtained. The film of the electrolyte thus obtained was cut into a disc of 1 cm in diameter, and put between a pair of stainless steel electrodes. The ionic conductivity was then determined by the above-described measuring method of ionic conductivity at 25° C. The electrolyte film was found to have ionic conductivity of 0.04 mS/cm, and in addition, had excellent strength.

Example 7

In a substantially similar manner to Example 6 except for the use of a polyolefin nonwoven fabric (50 μm thickness) as a reinforcing material, a polymer electrolyte of 60 μm thickness was obtained. The ion conductivity of the resulting electrolyte was determined by a similar measuring method. The resulting electrolyte film showed an ion conductivity of 0.04 mS/cm and in addition, had excellent strength.

Comparative Example 1

After polyethylene oxide (product of Fluka, 98%, average molecular weight: 1000) was dried by allowing it to stand for 4 days at 30° C. under reduced pressure of 1.3 kPa, it was dissolved in acetonitrile of the same amount to give a corresponding polymer solution. To the resulting polymer solution was added $LiPF_6$ in an amount to give a molar ratio (the number of moles of electrolytic salt)/(the total number of moles of ether oxygen atoms in polyethylene oxide) of 0.17 relative to the total number of moles of ether oxygen atoms of polyethylene oxide. Acetonitrile was distilled off from the solution to obtain a powder having an Li ion coordinated in polyethylene oxide. An electrolyte film was prepared by pressing the resulting powder. As a result of measurement, its ion conductivity was then found to be $6.3 \times 10^{-8}$ S/cm at 25° C., which was lower than that of any one of the electrolytes obtained in Examples.

Comparative Example 2

A boroxin-ring-having polymer electrolyte represented by the below-described formula (6) was obtained by adding 770 g (2.2 mol) of polyethylene glycol monomethyl ether having a molecular weight of 350 (product of Aldrich), 310 g (1.6 mol) of tetraethylene glycol (product of Aldrich) and lithium chloride to 3 mol of boric anhydride and heating to remove water which was the reaction by-product. The amount of lithium chloride was adjusted so that a molar ratio of a lithium chloride/boroxin ring of the boroxin compound thus formed be 0.5/1. As a result of measurement, the polymer electrolyte had an ion conductivity of $3.3 \times 10^{-8}$ S/cm at 25° C. and the transference number of Li ion was 0.88. The ion conductivity was lower than that of any one of the electrolytes obtained in Examples.

Examples and Comparative Examples so far described were summarized in Table 1. The polymer electrolytes according to the present invention are effective as an electrolyte for secondary batteries, particularly as an electrolyte for lithium secondary batteries.

TABLE 1

[Chemical formula 5]

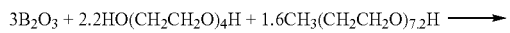

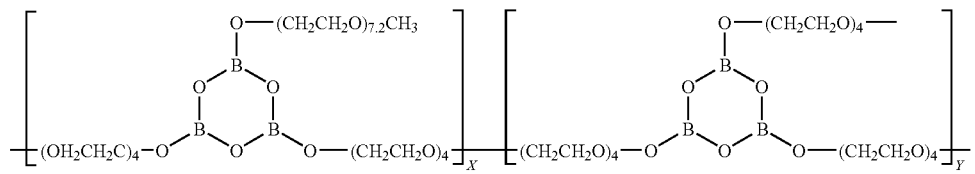

Formula (6)

| Ex. | X | m | n | Kind of salt | Ion conductivity (mS/cm) | Transference number of lithium ion |
|---|---|---|---|---|---|---|
| 1 | Absent | 5 | 5 | $LiN(CF_3SO_2)_2$ | 0.5 | 0.56 |
| 2 | Absent | 3 | 3 | $LiN(CF_3SO_2)_2$ | 1.0 | 0.51 |
| 3 | Phenylene | 5 | 5 | $LiN(CF_3SO_2)_2$ | 0.08 | 0.52 |
| 4 | Phenylene | 3 | 3 | $LiN(CF_3SO_2)_2$ | 0.05 | 0.50 |
| 5 | Phenylene | 3 | 3 | $LiN(CF_3SO_2)_2$ | 0.4 | 0.20 |
| 6 | Phenylene | 3 | 3 | $LiN(CF_3SO_2)_2$ | 0.04 | 0.45 |
| 7 | Phenylene | 3 | 3 | $LiN(CF_3SO_2)_2$ | 0.04 | 0.45 |
| Comp. Ex. 1 | — | | | $LiPF_6$ | 0.000025 | — |
| Comp. Ex. 2 | — | | | $LiN(CF_3SO_2)_2$ | 0.0006 | 0.88 |

Examples of a positive electrode which reversibly intercalates and deintercalates lithium in a lithium secondary battery include laminar compounds such as lithium cobaltate ($LiCoO_2$) and lithium nickelate ($LiNiO_2$), the above compounds substituted with one or more transition metals, and mixtures containing a lithium manganate [$Li_{1+x}Mn_{2-x}O_4$ (x=from 0 to 0.33), $Li_{1+x}Mn_{2-x-y}M_yO_4$ (in which M includes at least one metal selected from Ni, Co, Cr, Cu, Fe, Al and Mg, x=from 0 to 0.33, y=from 0 to 1.0, and 2−x−y>0), $LiMnO_3$, $LiMn_2O_3$, $LiMnO_2$, $LiMn_{2-x}M_xO_2$ (in which, M includes at least one metal selected from Co, Ni, Fe, Cr, Zn and Ta, and x=from 0.01 to 0.1), $Li_2Mn_3MO_8$ (in which, M includes at least one metal selected from Fe, Co, Ni, Cu and Zn)], copper-lithium oxide ($Li_2CuO_2$), a vanadium oxide such as $LiV_3O_8$, $LiFe_3O_4$, $V_2O_5$ or $Cu_2V_2O_7$, a disulfide compound, or $Fe_2(MoO_4)_3$.

As a negative electrode which reversibly intercalates and deintercalates lithium in a lithium secondary battery, usable are materials obtained by heat treating a natural graphite or a readily graphitizable material available from petroleum cokes, coal pitch cokes or the like at a temperature as high as 2500° C. or greater, mesophase carbon, amorphous carbon, carbon fibers, metals capable forming an alloy with lithium, and materials having a metal supported on the surface of carbon particles. Examples include metals selected from lithium, silver, aluminum, tin, silicon, indium, gallium and magnesium, and alloys thereof. Furthermore, these metals or oxides of them can be utilized as a negative electrode.

Although uses of the lithium ion secondary batteries of the present invention are not particularly limited, they can be used, for example, as power sources of IC cards, personal computers, large-sized electronic computers, notebook type personal computers, pen input personal computers, notebook type word processors, cellular phones, portable cards, watches, cameras, electric shavers, cordless phones, facsimiles, video, video cameras, electronic pocketbooks, desk electric calculators, electronic pocketbooks with communication functions, portable copying machines, liquid crystal televisions, electric tools, cleaners, game devices having functions such as virtual reality, toys, electric bicycles, walk assisting machines for medical care, wheelchairs for medical care, moving beds for medical care, escalators, elevators, forklifts, golf carts, power sources for emergency, load conditioners and power storage systems. Furthermore, they can be used for public use and also for war use and space use.

The present invention will hereinafter be described more specifically by examples. It should however be borne in mind that the present invention is not limited to or by them. In the examples, preparation of samples and evaluation of ionic conductivity were all carried out in an argon atmosphere unless otherwise specified. Moreover, in all the examples and comparative examples, concentration of the electrolytic salt was adjusted so that the molar ratio based on the total number of moles of ether oxygen atoms in the oxyalkylene group in the ion conductive polymer [(the number of moles of electrolytic salt)/(the total number of moles of ether oxygen atoms in oxyalkylene group)] be 0.03.

The polymer electrolytes used in Examples 8 to 13 are those prepared in Examples 1 to 7 and electrolytic salts are similar to those employed in Examples 1 to 6. Accordingly, Example 1, Example 2 and Examples 3 to 6 correspond to Example 8, Example 9 and Examples 10 to 13, respectively. The polymer electrolyte used in Comparative Example 3 is that prepared in Comparative Example 1, while the electrolytic salt of Comparative Example 3 is similar to that used in Comparative Example 1.

1. Preparation Examples of Electrodes

<Positive electrode> "CELLSEED" (trade name of lithium cobaltate; product Nippon Chemical Industrial Co., Ltd.), "SP270" (trade name of graphite; product of Japan Graphite Co., Ltd.) and "KF1120" (trade name of polyvinylidene fluoride; product of Kureha Chemical Industry Co., Ltd.) were mixed at a ratio of 80:10:10 in % by weight, and the mixture was poured into N-methyl-2-pyrrolidone, followed by mixing to prepare a slurry solution. The resulting slurry was coated on an aluminum foil of 20 μm thickness by the doctor blade method and dried. The coating amount of the mixture was 150 g/m². The aluminum foil was pressed to give a mixture bulk density of 3.0 g/cm³ and cut into 1 cm×1 cm to prepare a positive electrode. <Negative electrode> "CARBOTRON PE" (trade name of amorphous carbon; product of Kureha Chemical Industry Co., Ltd.) and "KF1120" (trade name of polyvinylidene fluoride; product of Kureha Chemical Industry Co., Ltd.) were mixed at a ratio of 90:10 in % by weight, and the mixture was poured into N-methyl-2-pyrrolidone, followed by mixing to prepare a slurry solution. The resulting slurry was coated on a copper foil of 20 μm thickness by the doctor blade method and dried. The coating amount of the mixture was 70 g/m². The resulting copper foil was pressed to give a mixture bulk density of 1.0 g/cm³, and cut into 1.2 cm×1.2 cm to prepare a negative electrode.

1. Method of Evaluation

<Charging and discharging conditions of battery> Charging and discharging were carried out at 25° C. and at a current density of 0.5 mA/cm² by using a charging and discharging device ("TOSCAT 3000", trade name; product of Toyo System Co., Ltd.). A constant current charging was carried out up to 4.2 V, and after the voltage reached 4.2 V, a constant voltage charging was carried out for 12 hours. Furthermore, a constant current discharging was carried out until a cut-off voltage of discharge reached 3.5 V. The capacity obtained by the first discharging was taken as an initial charge/discharge capacity.

Charging-discharging under the above conditions was regarded as 1 cycle, and the charging and the discharging were repeated until the capacity decreased to 70% or lower of the initial discharge capacity, and the number of repetition was taken as cycle characteristic. Furthermore, a constant current charging was carried out at a current density of 1 mA/cm² up to 4.2 V, and after the voltage reached 4.2 V, a constant voltage charging was carried out for 12 hours. Furthermore, a constant current discharging was carried out until a cut-off voltage of discharge reached 3.5 V. The resulting capacity and the initial cycle capacity obtained by the above charge and discharge cycle were compared, and the ratio was taken as a high-rate charge and discharge characteristics.

Example 8

The polymerizable composition solution obtained in Example 1 was cast over the positive electrode and negative electrode prepared by the above-described method and kept at 80° C. for 6 hours, whereby a polymer electrolyte was prepared thereover. These positive electrode and negative electrode were stacked one after another and kept at 80° C. for 6 hours under a load of 0.1 MPa. As illustrated in FIG. 1, stainless steel terminals 5 and 6 were then attached to positive electrode 1 and negative electrode 2, and they were inserted in a bag-shaped aluminum laminate film 7. The initial charge/discharge capacity of the battery thus obtained was 0.5 mAh, and the cycle characteristic was 50 times. The high rate discharge characteristic was 81%. When the aluminum laminate film was peeled off the battery, no fluidity of the electrolyte was observed inside the battery.

Example 9

The polymerizable composition solution obtained in Example 2 was cast over the positive electrode and negative electrode prepared by the above-described method and kept at 80° C. for 6 hours, whereby a polymer electrolyte was prepared thereover. These positive electrode and negative electrode were stacked one after another and adhered by keeping them at 80° C. for 6 hours under a load of 0.1 MPa. As illustrated in FIG. 1, stainless steel terminals 5 and 6 were then attached to positive electrode 1 and negative electrode 2, and they were inserted in a bag-shaped aluminum laminate film 7. The initial charge/discharge capacity of the battery thus obtained was 0.7 mAh, and the cycle characteristic was 70 times. The high rate discharge characteristic was 90%.

When the aluminum laminate film was peeled off the battery, no fluidity of the electrolyte was observed inside the battery.

Example 10

The polymerizable composition solution obtained in Example 3 was cast over the positive electrode and negative electrode prepared by the above-described method and kept at 80° C. for 6 hours, whereby a polymer electrolyte was prepared thereover. These positive electrode and negative electrode were stacked one after another and adhered by keeping them at 80° C. for 6 hours under a load of 0.1 MPa. As illustrated in FIG. 1, stainless steel terminals 5 and 6 were then attached to positive electrode 1 and negative electrode 2, and they were inserted in a bag-shaped aluminum laminate film 7. The initial charge/discharge capacity of the battery thus obtained was 0.3 mAh, and the cycle characteristic was 30 times. The high rate discharge characteristic was 50%. When the aluminum laminate film was peeled off the battery, no fluidity of the electrolyte was observed inside the battery.

Example 11

The polymerizable composition solution obtained in Example 4 was cast over the positive electrode and negative electrode prepared by the above-described method and kept at 80° C. for 6 hours, whereby a polymer electrolyte was prepared thereover. These positive electrode and negative electrode were stacked one after another and adhered by keeping them at 80° C. for 6 hours under of a load of 0.1 MPa. As illustrated in FIG. 1, stainless steel terminals 5 and 6 were then attached to positive electrode 1 and negative electrode 2, and they were inserted in a bag-shaped aluminum laminate film 7. The initial charge/discharge capacity of the battery thus obtained was 0.45 mAh, and the cycle characteristic was 40 times. The high rate discharge characteristic was 75%. When the aluminum laminate film was peeled off the battery, no fluidity of the electrolyte was observed inside the battery.

Example 12

The polymerizable composition solution obtained in Example 5 was cast over the positive electrode and negative electrode prepared in the above-described method and kept at 80° C. for 6 hours, whereby a polymer electrolyte was prepared thereover. These positive electrode and negative electrode were stacked one after another and adhered by keeping them at 80° C. for 6 hours under a load of 0.1 MPa. As illustrated in FIG. 1, stainless steel terminals 5 and 6 were then attached to positive electrode 1 and negative electrode 2, and they were inserted in a bag-shaped aluminum laminate film 7. The initial charge/discharge capacity of the battery thus obtained was 0.5 mAh, and the cycle characteristic was 50 times. The high rate discharge characteristic was 80%. When the aluminum laminate film was peeled off the battery, no fluidity of the electrolyte was observed in the battery.

Example 13

The polymerizable composition solution obtained in Example 6 was cast over the positive electrode and negative electrode prepared by the above-described method and kept in an atmosphere of pressure of 0.4 kPa and temperature of 80° C. for 6 hours to distill off the solvent, acetonitrile, whereby a polymer electrolyte was prepared over the positive and negative electrodes. The resulting positive electrode and negative electrode were stacked one after another and adhered by keeping them at 80° C. for 6 hours under a load of 0.1 MPa. As illustrated in FIG. 1, stainless steel terminals 5 and 6 were then attached to positive electrode 1 and negative electrode 2, and they were inserted in a bag-shaped aluminum laminate film 7. The initial charge/discharge capacity of the battery thus obtained was 0.5 mAh, and the cycle characteristic was 50 times. The high rate discharge characteristic was 80%. When the aluminum laminate film was peeled off the battery, no fluidity of the electrolyte was observed inside the battery.

Comparative Example 3

The polymerizable composition solution obtained in Comparative Example 1 was cast over the positive electrode and negative electrode prepared by the above-described method and kept in an atmosphere of pressure of 0.4 kPa and temperature of 80° C. for 6 hours to distill off acetonitrile from the solution, whereby an electrolyte was prepared over the positive electrode and negative electrode. The resulting positive electrode and negative electrode were stacked one after another and adhered by keeping them at 80° C. for 6 hours under a load of 0.1 MPa. As illustrated in FIG. 1, stainless steel terminals 5 and 6 were then attached to positive electrode 1 and negative electrode 2, and they were inserted in a bag-shaped aluminum laminate film 7. It was however impossible to carry out charging and discharging evaluation, at 25° C., of the battery thus prepared.

TABLE 2

| Examples | Initial charge/discharge capacity (mAh) | Cycle characteristic (times) | high rate discharge characteristic (%) Current density (1.0 mA/cm$^2$) |
|---|---|---|---|
| 8 | 0.5 | 50 | 81 |
| 9 | 0.7 | 70 | 90 |
| 10 | 0.3 | 30 | 50 |
| 11 | 0.45 | 40 | 75 |
| 12 | 0.5 | 50 | 80 |
| 13 | 0.5 | 50 | 80 |
| Comp. Ex. 3 | 0 | 0 | 0 |

The present invention is very useful when applied to lithium secondary batteries as described below.

(1) A lithium secondary battery equipped with positive and negative electrodes which reversibly intercalate and deintercalate lithium, and an electrolyte containing an ion conductive substance and an electrolytic salt, wherein the ion conductive substance is composed of a polymerizable boric compound represented by the formula (1).

(2) A lithium secondary battery, wherein the electrolyte is composed of a polymer obtained by polymerizing a polymerizable boric compound represented by the formula (1).

(3) A lithium second battery, wherein the electrolyte is composed of a polymer available by polymerizing a polymerizable boric compound represented by the formula (1) and a plasticizer.

(4) A lithium second battery, wherein the electrolytic salt is at least one of $LiPF_6$, $LiN(CF_3SO_2)_2$, $LiClO_4$, $LiBF_4$, $LiAsF_6$, $LiI$, $LiBr$, $LiSCN$, $Li_2B_{10}Cl_{10}$, and $LiCF_3SO_3$.

(5) A lithium secondary battery, wherein the electrolyte has been retained by a reinforcing material.

What is claimed is:

1. A polymerizable composition for electrochemical devices, which comprises an electrolytic salt and a polymerizable boric compound for electrochemical devices represented by the formula (1):

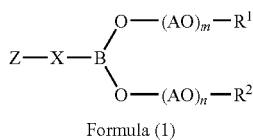

Formula (1)

wherein, B represents a boron atom, Z represents a polymerizable functional group selected from the group consisting of vinyl, allyl, methallyl, acryloyl and methacryloyl, X represents a divalent $C_{1-12}$ hydrocarbon group, or Z and B form a direct bond in the absence of X, AO represents a $C_{2-4}$ oxyalkylene group, m and n are each the number of moles of the oxyalkylene group added and each independently stands for 2 or greater but less than 6, and $R^1$ and $R^2$ each represents a $C_{1-12}$ hydrocarbon group.

2. A polymer electrolyte for electrochemical devices available by polymerizing a polymerizable composition as claimed in claim 1.

3. A polymer electrolyte for electrochemical devices according to claim 2, which comprises a plasticizer.

4. A polymer electrolyte according to claim 3, wherein the electrolytic salt is at least one of $LiPF_6$, $LiN(CF_3SO_2)_2$, $LiClO_4$, $LiBF_4$, $LiAsF_6$, LiI, LiBr, LiSCN, $Li_2B_{10}Cl_{10}$, and $LiCF_3SO_3$.

5. A secondary battery comprising a positive electrode having a terminal, a negative electrode having a terminal, and a polymer electrolyte as claimed in claim 3 sandwiched between said positive electrode and said negative electrode, the polymer electrolyte containing the electrolytic salt.

6. A polymer electrolyte according to claim 2, wherein the electrolytic salt is at least one of $LiPF_6$, $LiN(CF_3SO_2)_2$, $LiClO_4$, $LiBF_4$, $LiAsF_6$, LiI, LiBr, LiSCN, $Li_2B_{10}Cl_{10}$, and $LiCF_3SO_3$.

7. A secondary battery comprising a positive electrode having a terminal, a negative electrode having a terminal, and a polymer electrolyte as claimed in claim 6 sandwiched between said positive electrode and said negative electrode, the polymer electrolyte containing the electrolytic salt.

8. A polymer electrolyte for electrochemical devices according to claim 2, which has been retained in a reinforcing material.

9. A secondary battery comprising a positive electrode having a terminal, a negative electrode having a terminal, and a polymer electrolyte as claimed in claim 8 sandwiched between said positive electrode and said negative electrode, the polymer electrolyte containing the electrolytic salt.

10. A secondary battery comprising a positive electrode having a terminal, a negative electrode having a terminal, and a polymer electrolyte as claimed in claim 2 sandwiched between said positive electrode and said negative electrode, the polymer electrolyte containing the electrolytic salt.

* * * * *